US006740653B2

(12) United States Patent
Narayanan et al.

(10) Patent No.: US 6,740,653 B2
(45) Date of Patent: May 25, 2004

(54) SHELF LIFE EXTENSION OF MICROEMULSIONS CONTAINING ACTIVE AZA BIOCIDE

(75) Inventors: Kolazi S. Narayanan, Wayne, NJ (US); Domingo Jon, New York, NY (US)

(73) Assignee: ISP Investments Inc., Wilmington, DE (US)

( * ) Notice: Subject to any disclaimer, the term of this patent is extended or adjusted under 35 U.S.C. 154(b) by 164 days.

(21) Appl. No.: 10/023,013

(22) Filed: Dec. 18, 2001

(65) Prior Publication Data

US 2003/0119956 A1 Jun. 26, 2003

(51) Int. Cl.[7] .................. A01N 25/02; A01N 43/66; A01N 37/52
(52) U.S. Cl. ................ 514/241; 514/631; 514/637; 516/76; 424/405
(58) Field of Search ............... 516/76; 514/241, 514/631, 788, 637; 424/405

(56) References Cited

U.S. PATENT DOCUMENTS

| | | | |
|---|---|---|---|
| 5,188,832 A | * | 2/1993 | Mehlhorn et al. .......... 424/405 |
| 5,298,529 A | * | 3/1994 | Narayanan ................. 514/788 |
| 5,547,918 A | * | 8/1996 | Newton et al. ............. 424/405 |
| 5,968,990 A | * | 10/1999 | Jon et al. .................... 514/788 |
| 6,255,350 B1 | * | 7/2001 | Jon et al. .................... 514/588 |
| 6,479,438 B2 | * | 11/2002 | Narayanan et al. ......... 504/363 |

FOREIGN PATENT DOCUMENTS

WO     WO 01/60961 A1  *  8/2001

OTHER PUBLICATIONS

Milton J. Rosen, Surfactans and Interfacial phenomena (John Whiley & Sons, New York, NY, copyright 1978) pp. 224, May 1983.*

Sarmah, A. K., et al, "Hydrolysis of Trisulfuron, metsulfuron–methyl and chlorsulfuron in alkaline soil and aqueous solutions", Pest Management Science, vol. 56, No. 5, pp. 463–471 (2000—month unknown).*

* cited by examiner

*Primary Examiner*—Daniel S. Metzmaier
(74) *Attorney, Agent, or Firm*—Marilyn J. Maue; William J. Davis; Walter Katz

(57) ABSTRACT

This invention relates to the stabilization of o/w microemulsions containing an active aza biocide by addition of an alkaline, water soluble buffering agent in an amount sufficient to adjust the pH to between 6 and 14 and to the use of said o/w microemulsions to control infestations and/or infections when topically applied to livestock or domestic animals.

11 Claims, No Drawings

SHELF LIFE EXTENSION OF MICROEMULSIONS CONTAINING ACTIVE AZA BIOCIDE

FIELD OF THE INVENTION

The invention concerns increasing the shelf life of an oil-in-water (o/w) microemulsion containing a biocidally active aza type compound for repeated use over an extended period as a dip or spray in the control of animal, particularly livestock, infestations or infections and the o/w microemulsion compositions needed to achieve this improvement as well as prolonged aza activity.

BACKGROUND OF THE INVENTION

The treatment of animals by topical application of biocidal aza type o/w formulations, used as a dip, "pour on" or spray, are much in demand. Since the treatment of livestock, e.g. sheep, cattle, etc., requires repeated treatments over a long period to assure arrest of infestation or infection, it has been the practice to keep on hand sufficiently large quantities of the emulsion to cover the treatment period. As the solubility, and consequently the activity, of the aza compound is greatly improved in alkaline media, it has been the practice to add lime to the o/w emulsion. However, $Ca(OH)_2$ precipitates in the presence of air to form calcium carbonate, an insoluble, rock-like solid which settles to the bottom of the holding tank. The adsorption of significant quantities of the aza compound in the calcium carbonate accompanies the precipitation so that the biocidal activity in soluble form in the emulsion is greatly reduced. For example, it was found that lime-treated Amitraz microemulsion showed a 60% reduction in activity after only 6–14 days storage at about 20° C. At higher temperatures, 38° C. which are often encountered in the field, the depletion of soluble aza compound in the emulsion is even greater and more rapid.

Accordingly, it is an object of this invention to overcome the above disadvantages by significantly extending the shelf life and the efficacy of o/w microemulsions containing a biologically active aza component.

Another object is to provide an improved o/w microemulsion for protecting livestock and domestic animals against pest infestation such as lice, ticks, mites etc. and infections causing harmful dermal disorders, such as fungus infections, e.g. mange.

Still other objects are to provide an improved o/w microemulsion containing a biocidally active aza compound and to a method for preparing the improved microemulsion.

SUMMARY OF THE INVENTION

In accordance with this invention there is provided a stabilized reservoir of o/w microemulsion containing a biocidally active aza type compound by addition of an alkaline buffering agent such as an inorganic Na, K and or NH4 salt of a phenol, a polyphenol or a weak acid, preferably a polybasic acid; an alkanol amine, such as a polyalkanol amino $C_2$ to $C_4$ alkane, e.g. triethanol amino methane; a polyamine salt of a weak acid or a mixture of these buffering agents. The buffering agent, which is incorporated in the microemulsion without the assistance of any Ca salt, is added in an amount sufficient to adjust the pH of the microemulsion to between about 6 and 14, preferably, for Amitraz, to a pH of between 8 and 10 and a pH of between 6–8 for Metsulfurons.

DETAILED DESCRIPTION OF THE INVENTION

The active aza compounds referred to herein are active herbicidal or pesticidal compounds containing the aza group 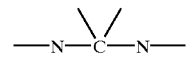 wherein the free valences on the carbon atom can form a double bond or are singly bonded to another atom or group. These aza bioactive agents include such compounds as Amitraz, Metsulfurons etc. containing the structure $R_1$—(X)—$R_2$ wherein one of $R_1$ and $R_2$ is a sulfur- and/or a nitrogen-containing heterocyclic radical having 3 to 5 carbon atoms in a 4 to 6 membered heterocyclic ring or alkenylphenyl, and the other of $R_1$ and $R_2$ is the same or is amidosulfuron, phenyl, sulfonylphenyl, phenyloxy, phenoxysulfonyl, or phenylamino where said phenyl radicals and heterocyclic radicals are optionally substituted with lower alkyl, halo, haloalkyl, cyano, $C_1$ to $C_4$ alkyl ether, a $C_1$ to $C_4$ ester, carboxy, ketone, and/or amino and X is or where $R_3$, $R_4$, $R_5$ and $R_6$ are each individually selected from the group of hydrogen, lower alkyl, cyano and amino. Specific examples of effective aza compounds are disclosed in U.S. Pat. No. 5,731,264 and are also incorporated herein by reference.

The active compounds of this invention contain an aza radical as defined above. Specific and preferred examples of such biologically or herbicidally active compounds include Amitraz, Metsulfuron-methyl, Metsulftron, Thifensulfron, Chlorsulfron, Sulfometuron and the like.

Amitraz has the structure:

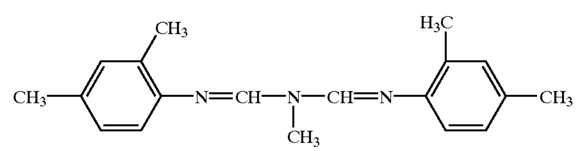

This insecticidal, acaricidal compound has a half life of about 6 hours in water at a pH of 7, and is soluble in water to the extent of 1 mg/liter.

The heterocyclic sulfonyl urea, Metsulfuron-methyl, having the structure and Metsulfuron having the structure

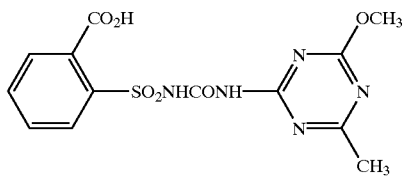

have similar half lives, as do other active aza compounds, such as sulfonyl urea (cyclosulfamuron) and those disclosed in U.S. Pat. No. 5,731,264. Of the above active compounds, Amitraz and Metasulfuron-methyl are most preferred.

The present buffering agents are added to an o/w microemulsion described and claimed in U.S. Pat. No. 6,255,350 the entire disclosure of which is incorporated herein by reference. The o/w microemulsion of this invention contains between about 0.01 and about 10 wt. % of the concentrate described in claim 1 of said issued patent which concentrate contains, by weight:

(a) between about 0.05 and about 25% of at least one active aza compound selected from the group consisting of Amitraz and an aza compound having the formula:

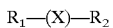

wherein one of $R_1$ and $R_2$ is alkenylphenyl, aminophenyl or a sulfur- and/or nitrogen-containing heterocyclic radical containing 3 to 5 carbon atoms in a 4 to 6 membered ring and the other of $R_1$ and $R_2$ is the same or is selected from the group consisting of amidosulfuron, phenyl, sulfonylphenyl, phenyloxy and phenyloxysulfonyl where said phenyl radicals and said heterocyclic radicals of $R_1$ and $R_2$ are optionally substituted with lower alkyl, halo, haloalkyl, cyano, $C_1$ to $C_4$ alkyl ether, $C_1$ to $C_4$ ester, carboxyl, ketone amido and amino and X is:

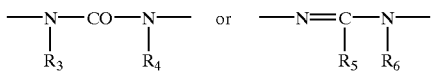

where $R_3$, $R_4$, $R_5$ and $R_8$ are each individually selected from the group consisting of hydrogen, lower alkyl, cyano, and amino, (b) between about 2 and about 40% of a lipophilic lactam selected from the group consisting of $C_8$ to $C_{18}$ N-alkyl pyrrolidone, $C_8$ to $C_{18}$ alkyl caprolactam and a mixture thereof, (c) between about 2 and about 20% of a moisture scavenging agent selected from the group consisting of a hindered carbopolyimide, a molecular sieve and a mixture thereof, (d) between about 10 and about 80% of a lipophilic/hydrophilic mixture of having an overall HLB of 7 to 20, comprising at least two emulsifiers wherein at least two of said emulsifiers in the mixture are non-ionic and (e) between 0 and about 15% of an aromatic oil.

After dilution of the concentrate with water, or water containing between about 0.001 and about 0.5 wt. % of salts such as the chlorides or sulfates of magnesium, calcium, iron etc. to form the microemulsion, between about 0.1 and about 1 wt. %, preferably 0.2–0.8 wt. %, based on total composition, of the present buffering agent is added. The microemulsions thus formulated with the present buffer replacing lime or other neutralizers, are stabilized with at least 95% aza activity retained over a period of at least a month up to 6 months or more.

The buffering agents employed herein, in addition to the specific examples recited above, include mixtures of sodium carbonate and sodium bicarbonate, sodium borate or perborate, sodium salts of other weak acids such as the polybasic acids represented by malonic, malic, glutaric, succinic and boric acids; sodium salts of phenols, e.g. cresol and polyphenols; amine salts of the foregoing acids; and the corresponding potassium or ammonium salts of the above sodium salts and mixtures of these buffering agents are also suitably employed in the o/w microemulsions of aza biocides. Of this group, the sodium carbonate/sodium bicarbonate 20/80-80/20 mixtures and corresponding potassium salt mixtures are most preferred. In general, the present o/w microemulsions contain between about 0.01 and about 5.0 wt. % of the buffering agent and between about 50 and about 500 ppm of the active aza component in the microemulsion. Preferably, 0.1–2 wt. % and most preferably 0.2–1 wt. % of the buffering agent is incorporated into the o/w emulsion to achieve a desirable pH. If desired, the pH can be further adjusted with NaOH or KOH which hydroxides are converted in the system to the corresponding carbonates.

Between about 1 and about 15 wt. % of an aromatic oil can also be added to the o/w microemulsion along with the buffer to further extend the microdroplets and the micellular structure. Suitable aromatic oils include alkyl naphthalenes, hydrogenated alkyl naphthalenes, vegetable oil and the like.

Having generally described the invention, reference is now had to the following examples which are presented to illustrate preferred embodiments but which are not to be construed as limiting to the scope of the invention as more broadly described above and defined in the appended claims.

EXAMPLE 1

Formation of the Concentrate

The ingredients shown in following Table A were mixed in a glass bottle for 60 minutes at room temperature using a magnetic stirrer.

TABLE A

| Ingredient | Wt. % |
| --- | --- |
| N-octyl pyrrolidone | 18.75 |
| Bis(diisopropyl phenyl carbodiimide (STABAXOL 1) | 8.63 |
| Amitraz (99% pure) | 6.25 |
| Castor oil ethoxylae (16 EO) | 36.60 |
| Sorbitan monooleate ethoxylate (TWEEN 80) | 26.28 |
| Sorbitol dissolved in glycerol | 3.48 |

The resulting homogeneous concentrate was recovered for further testing.

EXAMPLE 2

Formation of the Oil-In-Water (o/w) Microemulsion

One liter of 1000 ppm WHO (World Health Org.) hard water was mixed with 0.3% lime to provide an alkaline solution having a pH of 11.5–12. After one hour, 3.2 grams of the concentrate of Example 1 was added to the alkaline solution to produce a microemulsion having an initial Amitraz concentration of 200 ppm.

The water of the microemulsion was analyzed periodically for Amitraz content by extraction with acetonitrile prior to introduction into a HPLC (high performance liquid chromatography) column where, after storage at room temperature for 1–3 days, solid and supernate phases were separated by filtration and individually tested by acetonitrile extraction for Amitraz content. It was found that 25% of the Amitraz had been adsorbed on the Ca(OH)2/CaCO3 solid precipitate; thus reducing its availability. After 2 days analysis showed a reduction to 119 ppm Amitraz and, after one week, Amitraz was reduced to 90 ppm.

EXAMPLE 3

Formation of the o/w Microemulsion with the Present Buffer

Example 2 was repeated except that lime was replaced with an equal amount of reagent grade sodium carbonate, providing a pH of about 10.7. The resulting alkaline water solution was allowed to stand for 1 and 16 hours before adding 3.2 grams of the concentrate of Example 1 to produce the corresponding microemulsion having an initial Amitraz concentration of 200 ppm. The water of the microemulsion was analyzed in accordance with the method of Example 2 and the results are reported in following Table B.

TABLE B

| Sample | Time of Storage After Preparation | Standing time prior to Addition of Concentrate into buffered water | Remaining Amitraz, ppm |
|---|---|---|---|
| A | 2 days at 52° C.* | 1 hour | 182 |
| B | 2 days at 52° C.* | 16 hours | 193 |

*2 days at 52° C. is equivalent to ~2 months at room temperature.

After storage at room temperature for 1 month sample A lost only 7 ppm Amitraz and sample B lost only 5 ppm Amitraz.

EXAMPLE 4

Example 3 was repeated except that Na carbonate was replaced with a 1:3 mixture of Na carbonate/Na bicarbonate and the resulting o/w miroemulsion had a pH of 8.2. Amitraz was added after the alkaline solution had been allowed to stand for 16 hours. After 2 days storage at 52° C., the Amitraz content was reduced by only 15 ppm.

EXAMPLE 5

To 90 wt. % of the total buffered concentrate formulation described in Example 3, was added 10 wt. %, aromatic oil (aromatic EXXON 200). The aromatic oil preserved the microdroplets of the microemulsion for more than a month storage but did not affect or lower the stabilization of the active aza compound achieved with the present buffer.

The advantages of buffer in the present formulations, which include lowering the levels of haze and active component needed for a viable disinfectant solution and freeing the solution of hardened deposits due to the presence of lime, are apparent.

What is claimed is:

1. A stable o/w microemulsion comprising
   (i) between about 0.01 and about 10 wt. % of a concentrate formulation containing:
      (a) between about 0.05 and about 25 wt. % of at least one active aza compound selected from the group consisting of Amitraz and an aza compound having the formula:

$R_1—(X)—R_2$ wherein one of $R_1$ and $R_2$ is alkenyiphenyl, aminophenyl or a sulfur- and/or nitrogen-containing heterocyclic radical containing 3 to 5 carbon atoms in a 4 to 6 membered ring and the other of $R_1$ and $R_2$ is the same or is selected from the group consisting of amidosulfuron, phenyl, sulfonylphenyl, phenyloxy and phenyloxysulfonyl where said phenyl radicals and said heterocyclic radicals of $R_1$ and $R_2$ are optionally substituted with lower alkyl, halo, haloalkyl, cyano, $C_1$ to $C_4$ alkyl ether, $C_1$ to $C_4$ ester, carboxyl, ketone amido and amino and X is:

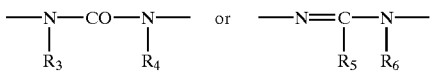

where $R_3$, $R_4$, $R_5$ and $R_6$ are each individually selected from the group consisting of hydrogen, lower alkyl, cyano, and amino,
      (b) between about 2 and about 40 wt. % of a lipophilic lactam selected from the group consisting of $C_8$ to $C_{18}$ N-alkyl pyrrolidone, $C_8$ to $C_{18}$ alkyl caprolactam and a mixture thereof,
      (c) between about 2 and about 20 wt. % of a moisture scavenging agent selected from the group consisting of a hindered carbopolyimide, a molecular sieve and a mixture thereof,
      (d) between about 10 and about 80 wt. % of a lipophilic/hydrophilic mixture of having an overall HLB of 7 to 20, comprising at least two emulsifiers wherein at least one of said emulsifiers in the mixture are non-ionic and
      (e) between 0 and about 15 wt. % of an aromatic oil;
   (ii) between about 90 and about 99.98 wt. % water and
   (iii) between about 0.01 and about 5 wt. % of an alkaline buffering agent selected from the group consisting of a Na, K and/or ammonium salt of a weak acid, a polyalkanol amino $C_1$ to $C_4$ alkane, a polyamine salt of a weak acid, a Na, K and/or ammonium salt of a phenol or polyphenol, an amine salt of a weak acid and a mixture of the foregoing buffering agents to adjust the pH of the microemulsion to 8–11.

2. The microemulsion of claim 1 wherein the buffering agent is a Na, K or ammonium salt of a weak acid selected from the group consisting of carbonic, malonic, malic, succinic, glutaric, boric acid and mixtures thereof.

3. The microemulsion of claim 2 wherein the buffering agent is a carbonate salt or a mixture of carbonate and bicarbonate salts.

4. The microemulsion of claim 2 wherein said salt is a sodium salt.

5. The microemulsion of claim 1 wherein the aza compound is selected from the group of a sulfuron and amitraz.

6. The microemulsion of claim 1 which contains between about 0.1 and about 2 wt. % of said buffering agent.

7. The microemulsion of claim 1 which contains between about 0.2 and about 1 wt. % of said buffering agent.

8. The microemulsion of claim 1 containing between about 0.02 and about 5.0 wt. % of said concentrate.

9. The microemulsion of claim 8 wherein said concentrate contains between about 8 and about 15 wt. % (a); between about 15 and about 30 wt. % (b); between about 7 and about 15 wt. % (c) and between about 65 and about 78 wt. % (d).

10. The application of the microemulsion of one of claims 1, 6, 7 or 9 in a biocidal amount to livestock by dip or by spray.

11. A stable o/w microemulsion comprising
    (i) between about 0.01 and about 10 wt. % of a concentrate formulation containing:
       (a) between about 0.05 and about 25 wt. % of at least one active aza compound selected from the group consisting of Amitraz and an aza compound having the formula:

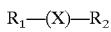

wherein one of $R_1$ and $R_2$ is alkenyiphenyl, aminophenyl or a sulfur- and/or nitrogen-containing heterocyclic radical containing 3 to 5 carbon atoms in a 4 to 6 membered ring and the other of $R_1$ and $R_2$ is the same or is selected from the group consisting of amidosulfuron, phenyl, sulfonyiphenyl, phenyloxy and phenyloxysulfonyl where said phenyl radicals and said heterocyclic radicals of $R_1$ and $R_2$ are optionally substituted with lower alkyl, halo, haloalkyl, cyano, $C_1$ to $C_4$ alkyl ether, $C_1$ to $C_4$ ester, carboxyl, ketone amido and amino and X is:

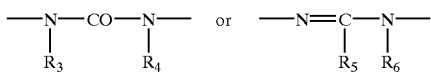

where $R_3$, $R_4$, $R_5$ and $R_6$ are each individually selected from the group consisting of hydrogen, lower alkyl, cyano, and amino,
(b) between about 2 and about 40 wt. % of a lipophilic lactam selected from the group consisting of $C_8$ to $C_{18}$ N-alkyl pyrrolidone, $C_8$ to $C_{18}$ alkyl caprolactam and a mixture thereof,
(c) between about 2 and about 20 wt. % of a moisture scavenging agent selected from the group consisting of a hindered carbopolyimide, a molecular sieve and a mixture thereof,
(d) between about 10 and about 80 wt. % of a lipophilic/hydrophilic mixture of having an overall HLB of 7 to 20, comprising at least two emulsifiers wherein at least one of said emulsifiers in the mixture are non-ionic;
(e) between 0 and about 15 wt. % of an aromatic oil selected from the group consisting of an alkyl naphthalene, a hydrogenated alkyl naphthalene and a mixture thereof;
(ii) between about 90 and about 99.98 wt. of water and
(iii) between about 0.01 and about 5 wt. % of an alkaline buffering agent selected from the group consisting of a Na, K and/or ammonium salt of a weak acid, a polyalkanol amino $C_1$ to $C_4$ alkane, a polyamine salt of a weak acid, a Na, K and/or ammonium salt of a phenol or polyphenol, an amine salt of a weak acid and a mixture of the foregoing buffering agents; and
wherein further added to extend said emulsion between about 5 and about 12 wt. % of an aromatic oil selected from the group consisting of an alkyl naphthalene, a hydrogenated alkyl naphthalene and a mixture thereof.

* * * * *